United States Patent
Schultz

(10) Patent No.: US 12,396,882 B2
(45) Date of Patent: Aug. 26, 2025

(54) THERMOREGULATION DEVICES AND METHODS

(71) Applicant: Joseph P. Schultz, Atlanta, GA (US)

(72) Inventor: Joseph P. Schultz, Atlanta, GA (US)

(*) Notice: Subject to any disclaimer, the term of this patent is extended or adjusted under 35 U.S.C. 154(b) by 1104 days.

(21) Appl. No.: 16/686,653

(22) Filed: Nov. 18, 2019

(65) Prior Publication Data

US 2020/0155342 A1 May 21, 2020

Related U.S. Application Data

(60) Provisional application No. 62/769,249, filed on Nov. 19, 2018.

(51) Int. Cl.
*A61F 7/00* (2006.01)
*A61F 7/02* (2006.01)
*B65D 81/18* (2006.01)
*B65D 81/38* (2006.01)

(52) U.S. Cl.
CPC ........... *A61F 7/007* (2013.01); *A61F 7/02* (2013.01); *B65D 81/18* (2013.01); *B65D 81/3888* (2013.01); *A61F 2007/0035* (2013.01); *A61F 2007/0036* (2013.01); *A61F 2007/0073* (2013.01); *A61F 2007/0086* (2013.01)

(58) Field of Classification Search
CPC ...... A61F 2007/0002; A61F 2007/0009; A61F 2007/0027; A61F 2007/0029; A61F 2007/0034; A61F 2007/0035; A61F 2007/0036; A61F 2007/0041; A61F 2007/0043; A61F 2007/0045; A61F 2007/0073; A61F 2007/0075; A61F 2007/0086; A61F 2007/0093; A61F 2007/0096; A61F 7/007; A61F 7/02; B65D 81/18; B65D 81/3888
See application file for complete search history.

(56) References Cited

U.S. PATENT DOCUMENTS

| | | | |
|---|---|---|---|
| 9,638,442 B2 | 5/2017 | Makansi et al. | |
| 10,058,476 B2 | 8/2018 | Baxter et al. | |
| 10,118,003 B2 | 11/2018 | Baxter et al. | |
| 2005/0075593 A1* | 4/2005 | Smith | A61F 5/028 602/2 |
| 2008/0223844 A1* | 9/2008 | Cronn | H05B 3/342 36/2.6 |
| 2008/0264464 A1* | 10/2008 | Lee | H10N 10/17 136/203 |
| 2013/0085552 A1* | 4/2013 | Mandel | A61F 7/007 607/99 |
| 2014/0260331 A1* | 9/2014 | Lofy | A61F 7/007 165/185 |

* cited by examiner

*Primary Examiner* — Tigist S Demie
(74) *Attorney, Agent, or Firm* — Merchant & Gould P.C.

(57) ABSTRACT

Methods and systems for thermoregulation of injured tissue, medical specimens and other perishable materials are disclosed. Thermoregulation systems can comprise a thermoelectric device comprising a thermoelectric element within a flexible sleeve such that the sleeve can be applied circumferentially within an orthopedic positioner. Methods for shipping medical specimens under precise temperature control are disclosed by actively regulating the temperature within containers and at the surface of the specimen. Methods for treating injured tissue that demonstrate increased precision and control are disclosed.

22 Claims, 9 Drawing Sheets

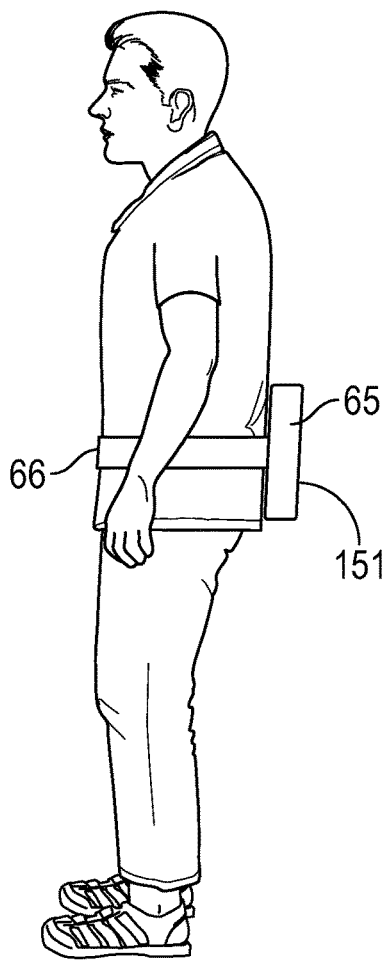
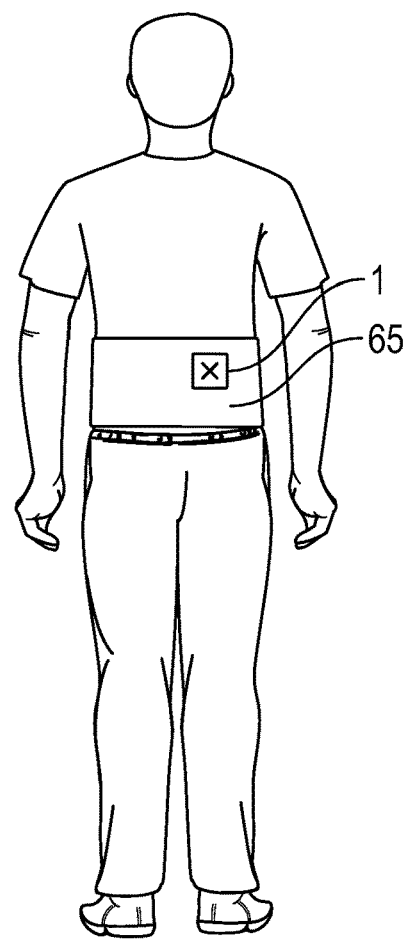
FIG. 4A  FIG. 4B
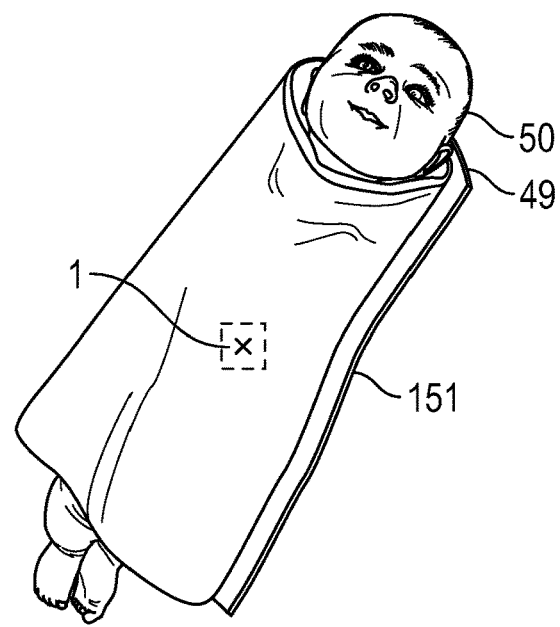
FIG. 5

THERMOREGULATION DEVICES AND METHODS

REFERENCE TO RELATED APPLICATION

This application claims the benefit of U.S. Provisional Patent Application No. 62/769,249, filed on Nov. 19, 2018, the disclosure of which is incorporated herein by reference in its entirety.

FIELD OF THE INVENTION

The present disclosure generally relates to treating injured tissue under and methods the transport of perishable items such as medical samples, under precise temperature control. More particularly, the present disclosure relates to the incorporation of thermoelectric devices into orthopedics and shipping containers to control the temperature for efficient medical treatment and transport.

BACKGROUND OF THE INVENTION

Methods for the precise and convenient regulation of temperature would be beneficial for many applications. Thermoelectric devices have been developed that transfer heat against equilibrium, and thus provide heating and cooling to one portion of the device as compared to another portion of the same device. These devices have previously been implemented in systems where heating or cooling is desired, but generally limited to flat inflexible devices (e.g., mattresses, seat covers) that cannot be applied circumferentially. Thermoregulation systems that incorporate flexible thermoregulation systems capable of alternately heating and cooling a body tissue or medical specimen would be beneficial to medical treatment and transport of medical samples.

SUMMARY

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

One aspect of the present invention is directed to a thermal orthopedic treatment system comprising a thermoelectric device, the thermoelectric device comprising an orthopedic positioner, a sleeve, and a panel comprising a plurality of thermoelectric elements. Each of the thermoelectric elements comprises a plurality of compacted conductors.

Methods for regulating temperature of tissues and substances using the thermoregulation devices and systems disclosed herein are also contemplated. For instance, a method for treating injured body tissue, pain or vascular disorders is disclosed, the method comprising applying a thermoelectric device to a body tissue, the device comprising a sleeve, an orthopedic positioner, and a panel comprising a plurality of thermoelectric elements, each of the thermoelectric elements comprising compacted conductors, and regulating the temperature of the body tissue.

Also disclosed herein are methods for shipping a perishable material comprising packaging the perishable material in a shipping container wherein the shipping container comprises a thermoelectric device, an insulator, and a panel comprising a plurality of thermoelectric elements, each of the thermoelectric elements comprising compacted conductors, regulating the temperature of the perishable material, and shipping the shipping container to a destination.

Both the foregoing summary and the following detailed description provide examples and are explanatory only. Accordingly, the foregoing summary and the following detailed description should not be considered to be restrictive. Further, features or variations can be provided in addition to those set forth herein. For example, certain aspects can be directed to various feature combinations and sub-combinations described in the detailed description.

BRIEF DESCRIPTION OF THE FIGURES

FIG. 4A depicts a back brace as an embodiment of a circumferential thermoregulation device.

FIG. 4B depicts a rear view of the back brace shown in FIG. 4A.

FIG. 5 depicts a blanket as an embodiment of a circumferential thermoregulation device.

DETAILED DESCRIPTION OF THE INVENTION

Figure 1A:
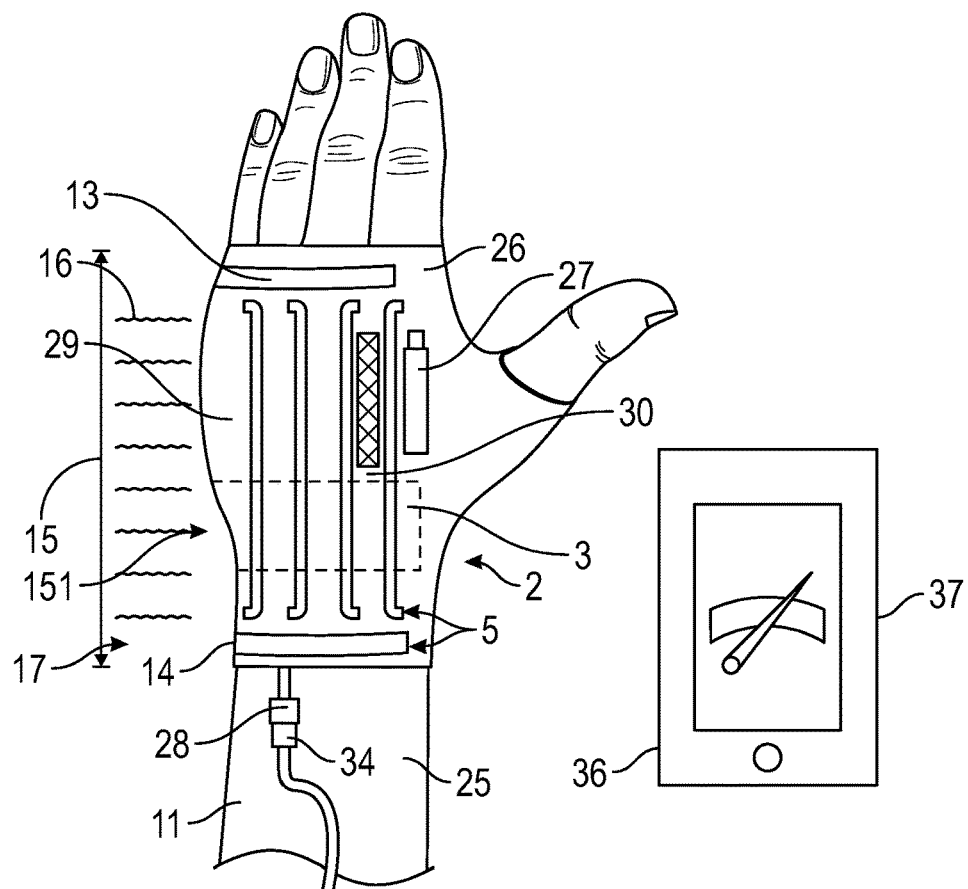
FIG. 1A depicts a wrist splint as an embodiment of a circumferential thermoregulation device.

Medical conditions sometimes require treatment with cold or heat. In particular, wounded or injured tissue from orthopedic injury can benefit from the application of cold therapy via ice packs and gel packs; and sometimes they can benefit from heat. Orthopedic injuries frequently requiring positioning such as bracing and immobilization to limit, reduce, prevent or eliminate movement of an injured area such as a joint or an extremity. Frequently heat and ice are recommended, but a patient may have a thick layer of an immobilizer such as a cast that prevents access to the inside body surfaces to apply heat or cold. Applying cold in the form of ice can moisten an immobilizer such as a non-waterproof cast or the webbing underneath and the skin tissue may become damaged due to the moist underventilated conditions. Inserting heat into a cast can lead to burns, if a hot object is insert into the cast and gets stuck or lost inside. Applying heat or cooling across the immobilzer is inefficient due to the complete width of material that must be traversed. Taking an immobilizer off to directly apply thermal therapy risks dislodgement of an injury that was maintained in position by the immobilzer or positioner. It can also be cumbersome to replace the previously removed device, particular when on an injured extremity; since the injury may limit motion and dexterity. Having separate wet icing devices that alternate with electrical devices can also be dangerous. Having to apply separate heating and cooling devices is also cumbersome, especially for one with an orthopedic extremity injury whose mobility and dexterity are already limited and their condition limits the ability to purchase, apply, remove, and reapply multiple devices for multiple techniques, especially those that may dangerously mix water from ice with heat from electricity or exothermic heat packs.

In addition, vibration in association with thermal therapy provides benefits in terms of distraction and pain. The benefit of vibration and/or cooling is believed to be achieved via the effects of the gate theory. Current cold therapy with vibration pain therapeutic devices with cooling elements have similar problems to cold therapy alone, as they require ice or gel packs that need to be refrozen to be "recharged". They cannot provide thermal therapy with the same unit without removing part of the device and or replacing part of the device. The temperature applied and the temperatures cannot be accurately regulated except by crude means such as removing ice when a unit is too cold. For heating devices, heat packs are removed when they get too hot. Devices of the prior at do not both heating and cooling in a regulated manner as a heat pack applied with an ice pack would cause the ice to melt. Further there is not a good way to measure the amount of heat or cold that is actually applied or the effect it has a body part such as injured extremity. There is also not a way to precisely titrate the amount of heat or cooling applied and to immediately counter the effect using the same device to achieve a desirable temperature, perfusion, or other medical end result, for example in an injured patient with an orthopedic injury to a joint or extremity. Devices and methods contemplated herein can include vibration elements and steps to assist therapy and relieve pain of injured tissue. The method of vibration is not limited to any particular type or element and can be generally any frequency, duration, and proximity relative to the injured tissue may be useful to the therapy and/or pain management of the injured tissue. U.S. Pat. Nos. 10,118,003 and 10,058,476 provide examples of such vibration methods and elements that can be compatible and beneficial to the thermoregulation systems and methods contemplated herein.

Embodiments of the present invention can comprise a single device that can provide orthopedic positioning to relieve pain, prevent motion and improve healing in combination with a single system that can provide both heating and cooling, especially in a sleeve form to provide circumferential therapy around a body surface such as an extremity, for example after orthopedic joint replacement surgery, to reduce swelling, improve blood flow, improve wound healing, reduce pain, prevent deep vein thrombosis by improving blood flow. Thermoelectric devices contemplated herein can also be used in conjunction with modular pumps such as those manufactured by Tempronics, Inc., Tucson, AZ In certain embodiments, devices may have at least one panel of a plurality of thermoelectric elements comprising compacted conductors as they are described recently in U.S. Pat. No. 9,638,442, incorporated herein by reference in its entirety.

Thermoregulation panels have previously been incorporated into large and bulky items, such as airline seat cushions, hospital mattresses, pet beds, and safety vests, to provide cooling and heating on flat surfaces. Such panels may be poorly suited for use in orthopedic devices. Wrapping a mattress around an orthopedic injury would be difficult and bulky. One could no longer sleep on the mattress and the device would be too large to be practical for use as an orthopedic restraint was it would not conform properly. Likewise, using a loose flexible vest garment would not provide the support and positioning required to prevent movement and rehabilitation. For example, an orthopedic injury to a midshaft radius and ulna fracture draped with a cooling vest would not be restrained and the four parts of the two bones would be unstable causing pain with movement. Furthermore none of the prior art teach the use of any of these technologies for regulated, controlled, programmed, protocolled therapies that involve circumferential application of heating and cooling elements in a single unit for orthopedic therapeutics particularly for traumatic orthopedic injuries or in a circumferential way using a sleeve. Certain embodiments of the invention may include a flexible sleeve to apply cool and or heat to the head. The sleeve may comprise a wrapped material such as a bandage. The sleeve may have a closed end such as a cap. The sleeve may be adjustable in size such as via an elastic construction or via adjustable straps that change the dimensions or pressure of the sleeve. The device might have thermal sensors that help provide a thermostatic control of the therapy. It may have other body function sensors such as EEG sensors, perfusion, oxygen, $CO_2$ or chemistry. In certain embodiments, the sleeve may comprise lights that help with safety and monitoring. The lights may be useful for applying light therapy for treatments such as hyperbilirubinemia of the newborn, psoriasis or for cosmetic purposes of tanning. The heat of the light therapy could be countered by the cooling of the sleeve or a panel. The therapy and or the heating and cooling may be on the inside of the sleeve, embedded in the sleeve wall, extending outside the sleeve or a combination of these conditions. This would enable a localized applied of heating or cooling to counteract the effects of another localized therapy inherently causing otherwise detrimental or undesirable heating or cooling effects.

For example the heat from phototherapy lights could be countered by the cooling of the thermoregulation circuitry within the same environment, and these both may be provide with the same system. A controller may be provided with the same device to operate each function in synchronized control by a single system. By counteracting the effects of one therapy, other interventions may be avoided. For example by using cooling from the same system that provides heated phototherapy to a newborn with hyperbilirubinemia, there would be less heat applied to the patient. If the patient is too hot there is more sweating, more metabolic demands and more fluid maintenance requirements to prevent dehydration. Reducing fluid requirements for a patient that may be having reduced or limited oral intake might avoid the need for intravenous fluid therapy and intravenous access. This would avoid the complications of IV therapy and would allow more sick infants to be treated safely at home rather than in hospitals where they would be more prone to nvosocomial infections and IV catheter associated blood stream infections that can be costly and deadly.

Other embodiments of the invention can comprise include a sleeve to apply cool and or heat to a perishable item during prolonged transport, such as a vaccine, a biologic culture, transplant organ or food product that is sensitive or labile. Such embodiments are able to maintain a product at a desired temperature through a variety of temperature extremes without being too hot or too cold. Certain embodiments comprise a flexible transport sleeve or container to provide more convenient packing and adaptability during packing and shipping. Alternatively, embodiments can comprise a rigid transport sleeve to prevent crushing of the inner contents or the construction could be a combination, such as a rigid outer shell. The sleeve may have a closed end or two closed ends. Embodiments contemplated herein can comprise a reusable opening such as a zipper or flap, tamper-evident, tamper-resistant or tamper-proof features to maintain the security of the contents, or any combination thereof. Benefits provided by these embodiments include logistic benefits to industries with temperature sensitive or labile products that require shipping. As a result, shipping to more distant locations than before is possible, therefore allowing benefits such as heat labile therapeutics to be sent to more remote areas than before, sampling of body fluids in remote regions reaching a specialized lab without degradation or permitting more centralized manufacturing, harvesting or storage of items before. A bag of chocolate with a rigid ball shell and more liquid interior might be sent from Southern California to Georgia during the summer by a multiday ground shipment without concern for the chocolate melting the spherical shell or ice turning the liquid chocolate center to an undesirable crystalline structure due to freezing with ice packs. Shipping can be done through more efficient standard carriers than more costly specialized carriers than before. The sleeve can comprise a wrapping material such as a bubble wrap, paper or foam.

In certain embodiments, the size of the sleeve may be adjustable such as via an elastic construction, via adjust sides or via adjustable straps that change the dimensions or pressure of the sleeve. Devices contemplated herein can have insulation to maintain the thermal effect applied. Alternatively, devices contemplated herein can have thermal sensors that help provide a thermostatic control of the therapy. Other embodiments can have other functions or sensors such as lights, cameras, motion detections, locators, identification elements. Such features can be present on the inside, embedded in the wall or the outside the sleeve. Additionally, embodiments may comprise other features that activate or inactivate the contents. For instance, certain embodiments can activate heat or cooling products based on a delivery route, including time and/or space via timers or geolocators, such near the end of a route a refrigerated food product can be heated for the recipient to receive a warm meal on arrival to the intended recipient. A lab specimen can have heat activated so that a culture that is initially preserved in a cold environment has growth accelerated with the geolocation or time specific activation that triggers an initial growth to set amount prior to delivery for a standardized evaluation by a lab.

Embodiments contemplated herein can be powered by a battery, a rechargeable battery, a wall outlet, a USB power source, a car cigarette lighter. Using car powered source would enable the device to be easily retrofitted to a vehicle for cooling of transported inner contents. Embodiments of contemplated herein comprising a sleeve can be applied to a car seat to provide localized heating or cooling of a seated occupant with the device restrained in a vertical position by a circumferential strap around the seat forming the sleeve. In such embodiments, the device can provide thermoregulation to the sleeve portion and might provide thermoregulation to an unsleeved portion. For example it is contemplated that a sleeved portion of a system might surround the front and back of the upright portion of a driver's seat of a car and another portion may lay over the horizontal portion of a driver's seat. Alternatively, another embodiment of the invention can be configured to lay completely open on a car seat, and be affixed to the seat by fastening or fasteners such as glue, tap, adhesive, hook and look, elastic, grommets or other fastening means. In such embodiments, the power source can be a cigarette lighter of a vehicle, or an outlet such as plug outlet on a plane. Applying the device to a seat in a vehicle in a retrofitted manner can save costs of construction of multiple different types of seats. A passenger is therefore able to bring their own thermoregulatory device for transport. Rather than providing a single ambient temperature in a vehicle cabin that may please most passengers, embodiments disclosed herein allow each passenger to regulate the temperature of their own seat to their preference. Providing a simple thermoregulator can save energy by efficiently transferring the heating or cooling to a person rather than changing the temperature of an entire vehicle cabin. Such arrangements allow vehicle occupants to avoid arguments, improve satisfaction, improve attitudes and improve travel safety.

One goal of the invention disclosed herein is to improve treatment of medical conditions that may require treatment with cold or heat, including wounded or injured tissue from orthopedic injury and those injuries requiring bracing and/or immobilization to limit, reduce, prevent or eliminate movement of an injured area. Embodiments disclosed herein can improve the application of heat and/or cooling therapy when impeded by immobilizer materials or to avoid the dangers of wet surface used with electrical devices, or to put heating and cooling into a single system that does not require removal of the device or parts of the device to change its nature or to perpetuate its effect over a prolonged period. Embodiments disclosed herein can include improved vibration devices that are combined with improved applications of heating or cooling for purposes such as treating orthopedic injuries. Embodiments disclosed herein can include improved thermoregulation systems that can provide a single system, such as a sleeve system that may provide circumferential therapy around a body surface such as an extremity, to improve therapy to reduce swelling, improve blood flow, improve wound healing, reduce pain and prevent deep vein thrombosis. Embodiments disclosed herein can include thermoregulatory systems such as with a device that may easily wrap, encircle and/or conform to a body part and may provide rigid immobilizing stability to a thermoregulated surface such as an injured extremity.

Protective suits such as sealed hermetically sealed hazmat suits are often heavier, less porous and have less ventilation than standard clothing, it would be desirable to have an improved protective suit with a thermoregulated system that could provide heating and or cooling as needed under extreme work conditions.

Embodiments disclosed herein can provide a non-uniform gradient via a thermoregulated system, for example to provide alternating therapies of heat and cooling, or to provide a gradient of heating in one part of the body with less heating in another part of the body; such as cooling to a leg, with less cooling to the toes to prevent distal injury due to distal circulatory insufficiency; or to provide more warmth to toes to increase circulation without providing too much warmth to a leg to prevent discomfort or hyperthermia. Embodiments disclosed herein can create gradients with a single panel of thermoelectric elements or a multiple panels in different spatial positions or with different uniform temperatures. Embodiments disclosed herein can operate as a system that provides a regulated, controlled, programmed, protocolled therapies that may involve circumferential application of heating and cooling elements in a single unit for orthopedic therapeutics particularly for traumatic orthopedic injuries or in a circumferential way using a sleeve to provide a predetermined amount of heating or cooling or maintain a predetermined temperature at a single or multiple body sites.

Contemplated herein are thermoregulated systems that effectively regulate the temperature of the head surface or regulate body temperature by regulating the amount of heating or cooling applied to the head, in circumstances such as being outdoors during summer or winter months or being in an operating room or emergency room where hypothermia therapies may be needed or hyperthermia may need to be reversed. Also contemplated herein are embodiments that have thermal sensors that help provide a thermostatic control of the therapy and/or sensors for other functions such as EEG sensors, perfusion, oxygen, CO2, chemistry, safety, monitoring, light therapy. Also contemplated herein are better systems for counteracting the effects of medical therapy causing heating or cooling with a counter effect provided by the device to maintain a desired outcome such as a desired body temperature, including having an improved system for phototherapy of newborns with jaundice.

Contemplated herein are better systems for transporting temperature sensitive items, including vaccines, a biologic specimens, transplant organs and food products, including transporting items and steady regulated temperature more easily and efficiently in smaller flexible containers, small rigid containers, containers with tamper benefits or heat or cold activated features that may be controlled via time or spatial sensors or regulators. Embodiments disclosed herein compose a better packaging system with protective material such as bubble wrap, paper or foam that provides some or all of the thermoregulatory features described. Improved better thermoregulation system are also contemplated herein that may have a sleeve and that may be adjustable in size, have an elastic construction; have two open ends, three closed ends, four closed ends or have insulation or have other functions or sensors such as lights, cameras, motion detections, locators, identification elements, or any combination thereof. These elements can be on the inside of the device, embedded in the wall or the outside of the device, or any combination thereof. In certain embodiments, other features may activate or inactivate the contents of a thermoregulated transport device, based on factors that may include time or space. In certain embodiments, the device is powered by a variety of sources such as a battery, a removable battery, rechargeable battery, a wall outlet, a usb power source, a vehicle cigarette lighter, or any combination thereof. In certain embodiments, the thermoregulation device can be easily retrofitted to a vehicle for cooling and heating of transported inner contents, including passengers so that individualized regulation for each passenger or portion of a compartment can be separately regulated, and may be retrofitted for individual regulation using a vehicular power source such as a cigarette lighter, usb port on a plane or two or three prong outlet in a vehicle. Certain embodiments may have a thin flexible thermoregulation device that can be restrained on a vertical surface of a vehicle and can be easily retrofitted and/or removed to a variety of vehicles or seats with a standard electrical connection.

Thermoregulation systems disclosed herein can have other features described that may lay completely flat and/or open on a car seat or be affixed by fastening or fasteners such as glue, tap, adhesive, hook and look, elastic, grommets or other fastening means and this may enable a seat in a vehicle to be retrofitted in manner would save costs of construction of multiple different types of seats and might provide individualized passenger preference and control may improve energy efficiency, comfort and travel safety.

Thermal orthopedic treatment systems to cure, mitigate, treat or prevent disease in man or animals are also contemplated herein. In certain embodiments, the treatment system can comprise a thermoelectric device comprising at least one orthopedic positioner, at least one sleeve and at least one panel of a plurality of thermoelectric elements comprising compacted conductors; wherein the panel can be a flexible panel. In other embodiments, the at least one panel of a plurality of thermoelectric elements comprising compacted conductors can comprise cooling elements for cooling the body; the at least one panel of a plurality of thermoelectric elements can comprise compacted conductors comprising cooling elements for cooling the body surface; or wherein the system comprises heating elements for warming the body; or wherein the system comprises cooling elements for cooling the body and heating elements for warming the body; or wherein the at least one panel of a plurality of thermoelectric elements comprising compacted conductors comprises cooling elements for providing thermal therapy to a portion of a body surrounded by the sleeve; or wherein the at least one panel of a plurality of thermoelectric elements comprising compacted conductors comprises cooling elements for providing thermal therapy to a portion of a body that is restrained by the orthopedic positioner; or wherein the at least one panel of a plurality of thermoelectric elements comprising compacted conductors comprises cooling elements for providing thermal therapy to a body extremity; or wherein the at least one panel of a plurality of thermoelectric elements comprising compacted conductors comprises cooling elements for cooling the body and heating elements for warming the body; or wherein the at least one panel of a plurality of thermoelectric elements comprising compacted conductors comprises cooling elements for cooling the body and heating elements for warming the body, comprises multiple panels of a plurality of thermoelectric elements to different positions around an axis of an extremity; or wherein the at least one panel of a plurality of thermoelectric elements comprising compacted conductors comprises a flexible material structured and arranged to circumferentially wrap around a portion of the body; or wherein the at least one panel of a plurality of thermoelectric elements comprising compacted conductors comprises a flexible material to continuously surround a portion of the body; or wherein the at least one panel of a plurality of thermoelectric elements comprising compacted conductors comprises a flexible material to circumferentially surround a portion of the body; or wherein the thermoelectric elements generate alternating cycles of heating and cooling in region of the device; or wherein the thermoelectric elements generate zones within the sleeve with variable amounts of heating or cooling; or wherein the thermoelectric elements generate zones within the sleeve with variable amounts of heating or cooling in response to the body surface temperature; or wherein the thermoelectric elements generate a thermal gradient along the longitudinal axis of the body surface; or wherein the thermoelectric elements generate a uniform body surface temperature within the sleeve; or wherein the thermoelectric elements have thermostatic control; or wherein the thermoelectric elements generate a programmed amount of heating or cooling; or wherein the devices comprises a strap; or wherein the devices comprises an adjustable positioning strap; or wherein the devices comprises an adjustable hook and look strap; or wherein the positioner comprises a responsive material that changes flexibility with changes in temperature or electrical current; or wherein the positioner comprises a brace; or wherein the positioner comprises a splint; or wherein the positioner comprises a cast; or wherein the device comprises a wound dressing; or wherein the device comprises a stocking; or wherein the device comprises a sock; or wherein the device comprises a compression stocking; or wherein the device fits around the hand; or wherein the device fits around the wrist; or wherein the device fits around the elbow; or wherein the device fits around the knee; or wherein the device fits around the ankle; or wherein the device fits around the foot; or wherein the device provides vibration; or wherein the device has a motor to provide vibration; or wherein the device has a thermometer; or wherein the device has safety illumination; or wherein the device fits around the head; or wherein the device comprises a shut off mechanism; or wherein the device comprises an alarm; or wherein the device is sterile; or wherein the device is water-resistant; or wherein the device is water-proof; or wherein the device comprises casting web material; or wherein the device comprises splinting web material; or wherein the device comprises exothermic casting or splinting material; or wherein the device comprises an internal body sensor; or wherein the device comprises a battery; or wherein the device comprises a rechargeable battery; or wherein the device comprises an electrical plug; or wherein the sleeve comprises smaller volume in the distal half of the sleeve compared to the proximal half of the sleeve; or wherein the device comprises a inner funneled configuration; or wherein the device comprises pressure sensors; or wherein the device comprises perfusion sensors; or wherein the device comprises oxygen sensors; or wherein the device comprises ischemia sensors; or wherein the device comprises padding; or wherein the device comprises padding within the sleeve; or wherein the at least one panel of a plurality of thermoelectric elements is embedded in padding; or wherein the at least one panel of a plurality of thermoelectric elements is in the sleeve; or wherein the at least one panel of a plurality of thermoelectric elements is in the brace; or wherein the at least one panel of a plurality of thermoelectric elements extend into the sleeve; or wherein the at least one panel of a plurality of thermoelectric elements extend outside of the sleeve; or wherein the device has wireless controller; or wherein the device has timer; or wherein the device is continuously powered on when continuously worn; or wherein the device has safety feature to prevent thermal injury; or wherein the device has safety feature to prevent thermal injury due to heat; or wherein the device has safety feature to prevent thermal injury due to cold; or wherein the device has safety feature to prevent thermal injury due to frostbite; or wherein the device has safety feature to prevent thermal injury due to temperatures less than or equal to 0 degrees centigrade; or wherein the device has safety feature to prevent thermal injury due to temperatures greater than or equal to 44 degrees centigrade; or wherein the device senses the ambient temperature of the environment to determine a targeted body temperature; or comprising a cover with thermally conductive materials selected from the group consisting of carbon fiber, gel, glycerin, metal particles and polyurethane; or, wherein the substrate material is thermally insulating; or, wherein the conducting sheet comprises a screen, a mesh, or a fabric; or wherein the screen, mesh, or fabric is metallized or comprised of metal or carbon; or, wherein the substrate material or the conducting sheet is stretchable in one or more dimensions; or, wherein heating and cooling is non-uniformly distributed within the sleeve; or, comprising thermoelectric string; or, comprising flexible circuit material; or, comprising thermoelectric string wherein the string utilizes flexible circuit material; or, comprising a thermoelectric system for heating or cooling, comprising: a panel comprising an electrically and thermally insulating material; and a plurality of thermoelectric elements comprising individual conductors that are (i) compacted in cross section inside the panel and (ii) expanded in at least one dimension outside the panel, wherein the individual conductors project away from and adjacent to a surface of the panel from one thermoelectric element to another thermoelectric element of the plurality of thermoelectric elements; or, comprising a thermoelectric system for heating or cooling, comprising: a panel comprising an electrically and thermally insulating material; and a plurality of thermoelectric elements comprising individual conductors that are (i) compacted in cross section inside the panel and (ii) expanded in at least one dimension outside the panel, wherein the individual conductors project away from and adjacent to a surface of the panel from one thermoelectric element to another thermoelectric element of the plurality of thermoelectric elements, wherein the plurality of thermoelectric elements comprises alternating n-type and p-type thermoelectric elements; or, comprising a thermoelectric system for heating or cooling, comprising: panels comprising an electrically and thermally insulating material; and a plurality of thermoelectric elements comprising individual conductors that are (i) compacted in cross section inside the panels and (ii) expanded in at least one dimension outside the panel, wherein the individual conductors project away from and adjacent to a surface of the panels from one thermoelectric element to another thermoelectric element of the plurality of thermoelectric elements; or, comprising a thermoelectric system for heating or cooling, comprising: panels comprising an electrically and thermally insulating material; and a plurality of thermoelectric elements comprising individual conductors that are (i) compacted in cross section inside the panels and (ii) expanded in at least one dimension outside the panel, wherein the individual conductors project away from and adjacent to a surface of the panels from one thermoelectric element to another thermoelectric element of the plurality of thermoelectric elements, wherein the plurality of thermoelectric elements comprises alternating n-type and p-type thermoelectric elements; or, comprising a thermoelectric module that pumps heat reversibly from one side to another side when energized with a voltage.

Also contemplated herein are thermoelectric devices comprising at least one at least one panel of a plurality of thermoelectric elements comprising compacted conductors, wherein a first panel of a plurality of thermoelectric elements that function to provide heating and cooling elements and the device is structured and arranged fit around the head; a thermoelectric device comprising at least one at least one panel of a plurality of thermoelectric elements comprising compacted conductors, wherein a first panel of a plurality of thermoelectric elements that function to provide cooling elements and the first panel can by divided into a functioning smaller second panel of thermoelectric elements; a thermoelectric device comprising at least one at least one panel of a plurality of thermoelectric elements comprising compacted conductors, wherein a first panel of a plurality of thermoelectric elements that function to provide cooling elements and the first panel can by divided into a functioning smaller second panel of thermoelectric elements and a functioning smaller third panel of thermoelectric elements; a thermoelectric device comprising at least one at least one panel of a plurality of thermoelectric elements comprising compacted conductors, wherein a first panel of a plurality of thermoelectric elements can by divided into smaller second and third panels of thermoelectric elements; a plurality of thermoelectric components with couplers to connect a thermoelectric component with at least one or two other thermoelectric components in a serial arrangement; a plurality of thermoelectric components with couplers to connect a thermoelectric component with at least two other thermoelectric components in a serial arrangement; a plurality of thermoelectric components with couplers to connect a thermoelectric component with at least one or two other thermoelectric component couplers in a serial arrangement; a plurality of thermoelectric components with couplers to connect a thermoelectric component with at least two other thermoelectric component couplers in a serial arrangement; a plurality of thermoelectric panels of a plurality of thermoelectric elements comprising compacted conductors, wherein a panels are in a series and comprise at least one coupler to couple the panels to each other; a plurality of thermoelectric panels of a plurality of thermoelectric elements comprising compacted conductors, wherein a panels are in a series and comprise at least two couplers to couple the panels to each other; a plurality of thermoelectric panels of a plurality of thermoelectric elements comprising compacted conductors, wherein the panels are in a series and comprise at least three couplers to couple the panels to each other; a plurality of thermoelectric panels of a plurality of thermoelectric elements comprising compacted conductors, wherein a segment can be uncoupled from a proximal coupler and distal coupler and the proximal and distal couplers can be coupled to provide thermoelectric heating or cooling without the removed segment; a thermoelectric device comprising at least one at least one panel of a plurality of thermoelectric elements comprising compacted conductors, wherein a first panel of a plurality of thermoelectric elements can by divided into smaller second and third panels of thermoelectric elements; a thermal orthopedic treatment system to cure, mitigate, treat or prevent disease in man or animals, the treatment system comprising: a thermoelectric device comprising at least one sleeve and at least one panel of a plurality of thermoelectric elements comprising compacted conductors; a thermal orthopedic treatment system to cure, mitigate, treat or prevent disease in man or animals, the treatment system comprising a thermoelectric device comprising at least one orthopedic positioner and at least one panel of a plurality of thermoelectric elements comprising compacted conductors; a thermal orthopedic treatment system to cure, mitigate, treat or prevent disease in man or animals, the treatment system comprising: a thermoelectric device comprising at least one sleeve and at least one panel of a plurality of thermoelectric elements comprising compacted conductors with cooling elements for cooling the body and heating elements for warming the body; a thermal orthopedic treatment system to cure, mitigate, treat or prevent disease in man or animals, the treatment system comprising: a thermoelectric device comprising at least one orthopedic positioner and at least one panel of a plurality of thermoelectric elements comprising compacted conductors with cooling elements for cooling the body and heating elements for warming the body.

Also contemplated herein are methods of treating injured body tissue, the method comprising the steps of a thermoelectric device comprising at least one orthopedic positioner and at least one panel of a plurality of thermoelectric elements comprising compacted conductors to a body surface; or a method of treating vascular insufficiency, the method comprising the steps of applying a thermoelectric device comprising at least one orthopedic positioner, at least one sleeve and at least one panel of a plurality of thermoelectric elements comprising compacted conductors; or a method of treating injured body tissue, the method comprising the steps of a thermoelectric device comprising at least one panel of a plurality of thermoelectric elements comprising compacted conductors to a body surface; or a method of treating injured body tissue, the method comprising the steps of a thermoelectric device comprising at least one sleeve and at least one panel of a plurality of thermoelectric elements comprising compacted conductors to a body surface; or a method of treating injured body tissue, the method comprising the steps of applying a thermoelectric device comprising at least one orthopedic positioner, at least one sleeve and at least one panel of a plurality of thermoelectric elements comprising compacted conductors; or a method of treating injured body tissue, the method comprising the steps of applying a thermoelectric device comprising at least one orthopedic positioner, at least one sleeve and at least one panel of a plurality of thermoelectric elements comprising compacted conductors with heating and cooling capabilities to maintain a body surface at predetermined temperature; or a method of preventing deep vein thrombosis, the method comprising the steps of applying a thermoelectric device comprising at least one orthopedic positioner, at least one sleeve and at least one panel of a plurality of thermoelectric elements comprising compacted conductors with heating and cooling capabilities to maintain a body surface at predetermined temperature; or a method of treating a wound, the method comprising the steps of applying a thermoelectric device comprising at least one orthopedic positioner, at least one sleeve and at least one panel of a plurality of thermoelectric elements comprising compacted conductors; or a method of thermoregulation of body temperature, the method comprising the steps of applying a thermoelectric device comprising at least one head band and at least one panel of a plurality of thermoelectric elements comprising compacted conductors with heating and cooling elements; or a method of treating a wound, the method comprising the steps of applying a thermoelectric device comprising at least one orthopedic positioner, at least one sleeve and at least one panel of a plurality of thermoelectric elements comprising compacted conductors capable of providing cooling and heating and selectively applying heat or cooling to a body surface in response to a body temperature; or a method of treating a wound, the method comprising the steps of applying a thermoelectric device comprising at least one orthopedic positioner, at least one sleeve and at least one panel of a plurality of thermoelectric elements comprising compacted conductors capable of providing cooling and heating and selectively applying a similar amount heat or cooling in circumferential distribution to a body extremity; or a method of treating a wound, the method comprising the steps of applying a thermoelectric device comprising at least one orthopedic positioner, at least one sleeve and at least one panel of a plurality of thermoelectric elements comprising compacted conductors capable of providing cooling and heating and selectively applying a first uniform amount heat or cooling in circumferential distribution to a body extremity and applying a second uniform amount heat or cooling in circumferential distribution to a body extremity, wherein the first uniform amount of heating or cooling in a circumferential distribution is different from the second uniform amount of heating or cooling in a circumferential distribution to generate a thermal gradient; or a method of treating a wound, the method comprising the steps of applying a thermoelectric device comprising at least one orthopedic positioner, at least one sleeve and at least one panel of a plurality of thermoelectric elements comprising compacted conductors capable of providing cooling and heating and generating a thermal gradient along the axis of an extremity by applying thermostatically controlled thermoregulation to different regions of the body surface; or a method of treating a wound, the method comprising the steps of applying a thermoelectric device comprising at least one orthopedic positioner, at least one sleeve and at least one panel of a plurality of thermoelectric elements comprising compacted conductors capable of providing cooling and heating and applying heat or cooling to a body surface in response to a body temperature within the sleeve; or a method of treating a wound, the method comprising the steps of applying a thermoelectric device comprising at least one orthopedic positioner, at least one sleeve and at least one panel of a plurality of thermoelectric elements comprising compacted conductors capable of providing cooling and heating and applying heat or cooling to a body surface in response to a body surface temperature within the sleeve; or a method of treating a wound, the method comprising the steps of applying a thermoelectric device comprising at least one orthopedic positioner, at least one sleeve and at least one panel of a plurality of thermoelectric elements comprising compacted conductors capable of providing cooling and heating and applying heat or cooling to a body surface in response to a deep body temperature below the surface of the body within the sleeve; or a method of treating a wound, the method comprising the steps of applying a thermoelectric device comprising at least one orthopedic positioner, at least one sleeve and at least one panel of a plurality of thermoelectric elements comprising compacted conductors capable of providing cooling and heating and applying heat or cooling to a body surface in response to a thermometer reading outside of the sleeve; or a method of treating a wound, the method comprising the steps of applying a thermoelectric device comprising at least one orthopedic positioner, at least one sleeve and at least one panel of a plurality of thermoelectric elements comprising compacted conductors capable of providing cooling and heating and applying heat or cooling to a body surface in response to a measured non thermal body parameter including perfusion, color, pain, pressure; or a method of treating a wound, the method comprising the steps of applying a thermoelectric device comprising at least one orthopedic positioner, at least one sleeve and at least one panel of a plurality of thermoelectric elements comprising compacted conductors capable of providing cooling and pressure regulator for regulating pressure within the sleeve; or a method of treating a post-surgical orthopedic patient, the method comprising the steps of applying a thermoelectric device comprising at least one orthopedic positioner, at least one sleeve and at least one panel of a plurality of thermoelectric elements comprising compacted conductors capable of providing cooling; or a method of treating a post-surgical orthopedic patient, the method comprising the steps of applying a thermoelectric device comprising at least one orthopedic positioner, at least one sleeve and at least one panel of a plurality of thermoelectric elements comprising compacted conductors capable of providing cooling and heating; or a method of treating a post-surgical orthopedic patient, the method comprising the steps of applying a thermoelectric device comprising at least one orthopedic positioner, at least one sleeve and at least one panel of a plurality of thermoelectric elements comprising compacted conductors capable of providing cooling and heating in a predetermined protocol; or a method of treating a post-surgical orthopedic patient, the method comprising the steps of applying a thermoelectric device comprising at least one orthopedic positioner, at least one sleeve and at least one panel of a plurality of thermoelectric elements comprising compacted conductors capable of providing cooling and heating in a predetermined protocol with adjustments made to maintain a desired temperature; or a method of treating a post-surgical orthopedic patient, the method comprising the steps of applying an adjustable thermoelectric device comprising at least one orthopedic positioner, at least one sleeve and at least one panel of a plurality of thermoelectric elements comprising compacted conductors capable of providing cooling and heating in a predetermined protocol with adjustments made to maintain a desired temperature, wherein the size of the sleeve is adjustable to conform to changes in the diameter of a swollen extremity after the application of heating or cooling; or method of treating a post-surgical orthopedic patient, the method comprising the steps of applying an adjustable thermoelectric device comprising at least one orthopedic positioner, at least one sleeve and at least one panel of a plurality of thermoelectric elements comprising compacted conductors capable of providing cooling and heating in a predetermined protocol with adjustments made to maintain a desired temperature, wherein the pressure of the sleeve on the body surface is adjustable to conform to changes in the diameter of a swollen extremity after the application of heating or cooling; or a method of treating injured body tissue, the method comprising the steps of applying a thermoelectric device comprising at least one orthopedic positioner, at least one sleeve and at least one panel of a plurality of thermoelectric elements comprising compacted conductors capable of providing cooling and heating and on one side of an extremity to create a thermal gradient along an opposite second side of the extremity; or a method of treating injured body tissue, the method comprising the steps of applying a thermoelectric device comprising at least one orthopedic positioner, at least one sleeve and at least one panel of a plurality of thermoelectric elements comprising compacted conductors capable of providing cooling on one side of an extremity and providing heat along an opposite second side of the extremity to provide thermal gradient; or a method of treating injured body tissue, the method comprising the steps of applying a thermoelectric device comprising at least one orthopedic positioner, at least one sleeve and at least one panel of a plurality of thermoelectric elements comprising compacted conductors capable of providing cooling on one side of an extremity and providing heat along an opposite second side of the extremity to provide thermal gradient greater than can be achieved by applying heating or cooling only to one side of the extremity; or a method of treating injured body tissue, the method comprising the steps of applying a thermoelectric device comprising at least one orthopedic positioner, at least one sleeve and at least one panel of a plurality of thermoelectric elements comprising compacted conductors capable of providing cooling and heating and on a side of an extremity to create a thermal gradient along the opposite side of the extremity; or a method of treating injured body tissue, the method comprising the steps of applying a thermoelectric device comprising at least one orthopedic positioner, at least one sleeve and at least one panel of a plurality of thermoelectric elements comprising compacted conductors capable of providing cooling and heating and creating a body surface temperature that is preprogrammed to vary the application of heat or cold with time; or a method of treating injured body tissue, the method comprising the steps of applying a thermoelectric device comprising at least one orthopedic positioner, at least one sleeve and at least one panel of a plurality of thermoelectric elements comprising compacted conductors capable of providing cooling and heating and creating a body surface temperature that is preprogrammed to apply cooling for at least 12 hours before applying heat; or a method of treating injured body tissue, the method comprising the steps of applying a thermoelectric device comprising at least one orthopedic positioner, at least one sleeve and at least one panel of a plurality of thermoelectric elements comprising compacted conductors capable of providing cooling and heating and creating a body surface temperature that is preprogrammed to apply cooling and then apply heating after no sooner than a predetermined interval after the device has begun cooling; or a method of treating injured body tissue, the method comprising the steps of applying a thermoelectric device comprising at least one orthopedic positioner, at least one sleeve and at least one panel of a plurality of thermoelectric elements comprising compacted conductors capable of providing cooling and heating and creating a body surface temperature that is preprogrammed to apply cooling and then apply heating after no sooner than a 72, 48, 24, 12 hours after the device has begun cooling; or a combination of these.

Also contemplated herein are orthopedic positioners comprising a sleeve and a thermoelectric device comprising a panel formed of a substrate material that is electrically insulating, and having a plurality of thermoelectric elements comprising compacted conductors located at least in part inside the substrate material and expanded conductors located at least in part outside the substrate material, wherein the panel is covered by a conducting sheet that diverts leakage current; or a sleeve comprising an orthopedic positioner and a thermoelectric device comprising a panel formed of a substrate material that is electrically insulating, and having a plurality of thermoelectric elements comprising compacted conductors located at least in part inside the substrate material and expanded conductors located at least in part outside the substrate material, wherein the panel is covered by a conducting sheet that diverts leakage current; or an orthopedic brace comprising a sleeve and a thermoelectric device comprising a panel formed of a substrate material that is electrically insulating, and having a plurality of thermoelectric elements comprising compacted conductors located at least in part inside the substrate material and expanded conductors located at least in part outside the substrate material, wherein the panel is covered by a conducting sheet that diverts leakage current; or a thermoelectric device comprising at least one orthopedic positioner, at least one sleeve and a thermoelectric device comprising a panel formed of a substrate material that is electrically insulating, and having a plurality of thermoelectric elements comprising compacted conductors located at least in part inside the substrate material and expanded conductors located at least in part outside the substrate material, wherein the panel is covered by a conducting sheet that diverts leakage current; or an orthopedic positioner comprising a sleeve and a thermoelectric device comprising a panel formed of a substrate material that is electrically insulating, and having a plurality of thermoelectric elements comprising compacted conductors located at least in part inside the substrate material and expanded conductors located at least in part outside the substrate material, wherein the panel is covered by a conducting sheet that diverts leakage current, and wherein the panel is produced in an automated fashion by machines that perform one or more of the following operations: wire cutting, wire crimping, tinning, picking and placing of thermoelectric elements, dispensing or stenciling of solder or solder paste, solder reflow, singulation, and puncture of the insulating layer with an array of hollow needles; or an orthopedic positioner comprising a sleeve and a thermoelectric device comprising a panel formed of a substrate material that is electrically insulating, and having a plurality of thermoelectric elements comprising compacted conductors located at least in part inside the substrate material and expanded conductors located at least in part outside the substrate material, wherein the panel is covered by a conducting sheet that diverts leakage current, and wherein the panel is produced in an automated fashion by machines that perform one or more of the following operations: flex circuit patterning by etching or punching, robotic picking and placing of elements, dispensing of solder or solder paste, solder reflow, and puncture of the insulating layer with hollow needles; or an orthopedic positioner comprising a brace, a sleeve and a thermoelectric device comprising a panel comprising a panel formed of a substrate material that is electrically insulating, and having a plurality of thermoelectric elements comprising compacted conductors located at least in part inside the substrate material and expanded conductors located at least in part outside the substrate material, wherein the panel is covered by a conducting sheet that diverts leakage current, and further comprising a wireless power transmitter and receiver for powering the device; or an orthopedic positioner comprising a sleeve and a thermoelectric system comprising a cushion comprising a thermoelectric panel mounted on top of an airflow layer comprising a porous cover combined with a blower fan, to blow air into the sleeve; or an orthopedic positioner comprising a sleeve and a thermoelectric system with expanded conductors positioned internally within the sleeve; or an orthopedic positioner comprising a sleeve and a thermoelectric system compacted conductors that are not positioned internally within the sleeve; or a system comprising an orthopedic positioner, a sleeve and a plurality of panels that are arranged to be selectively turned on and off to provide more or less cooling or heating in response to pressure, temperature, perfusion, pain or color, or a combination thereof, wherein an individual panel of the plurality of panels is formed of a substrate material that is electrically insulating, and includes a plurality of thermoelectric elements comprising compacted conductors located at least in part inside the substrate material and expanded conductors located at least in part outside the substrate material, wherein the individual panel is covered by a conducting sheet that diverts leakage current; or a combination of these.

Figure 1B:
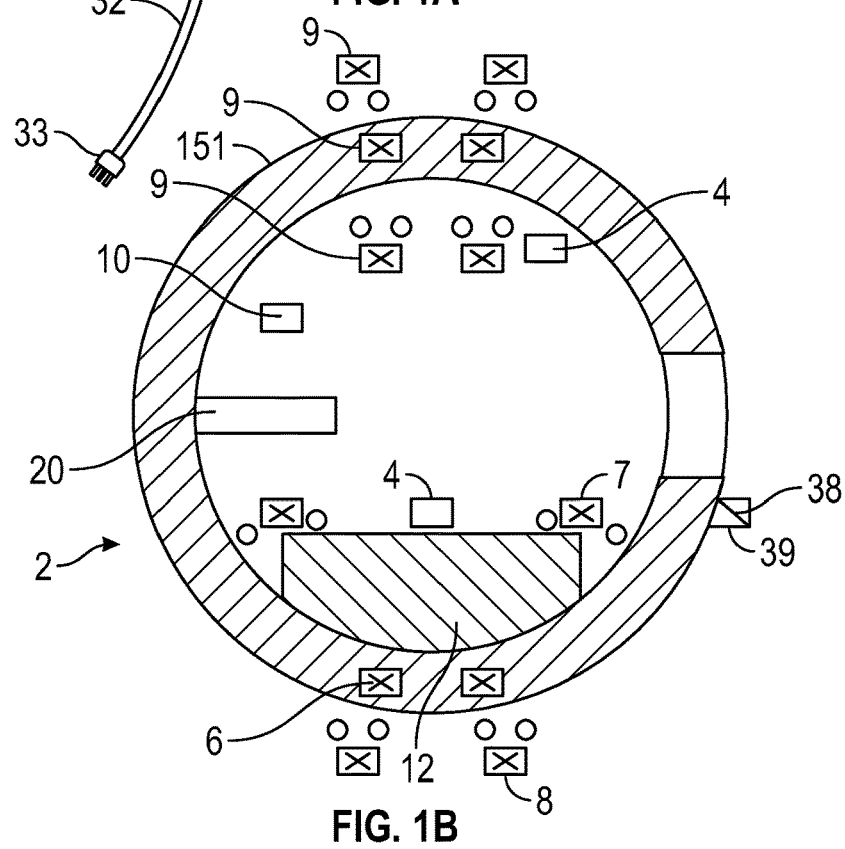
FIG. 1B depicts an axial view of the wrist splint shown in FIG. 1A.
Figure 2A:
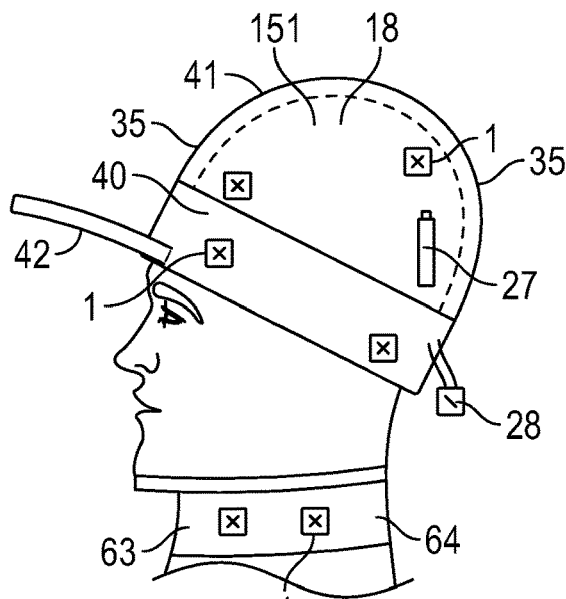
FIG. 2A depicts a hat as an embodiment of a circumferential thermoregulation device.
Figure 2B:
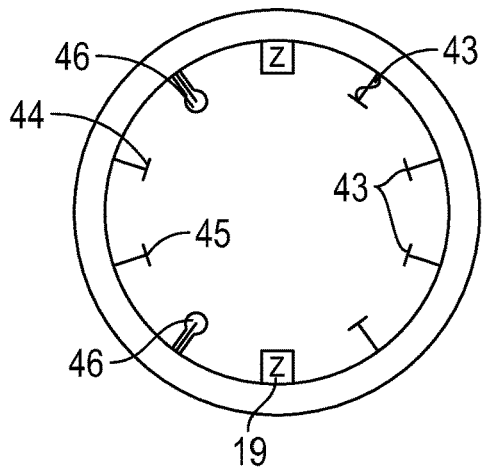
FIG. 2B depicts an axial view of the hat shown in FIG. 2B.
Figure 3A:
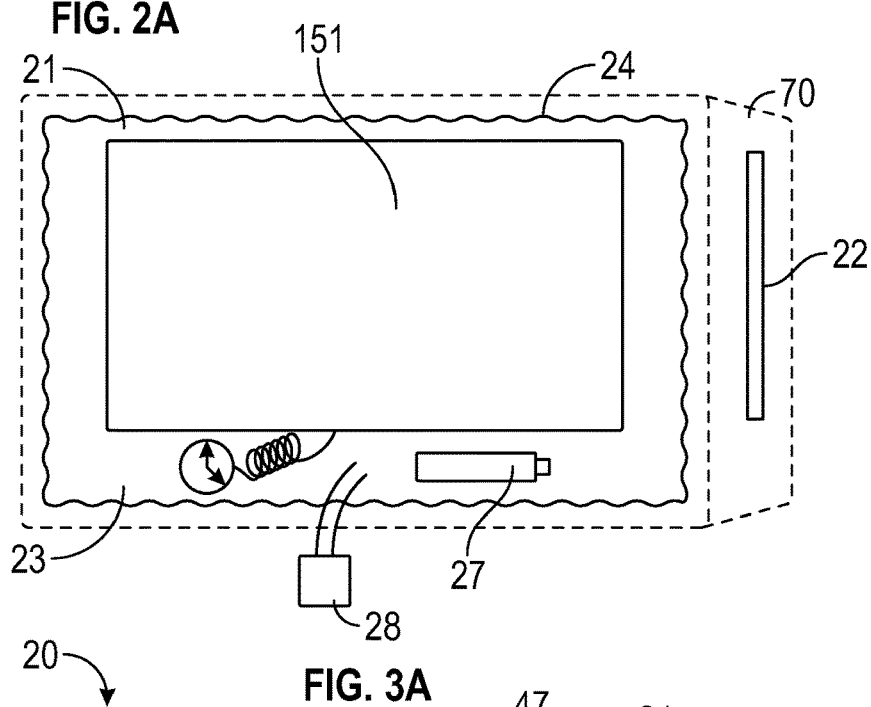
FIG. 3A depicts a shipping container as an embodiment of a thermoregulation device.
Figure 3B:
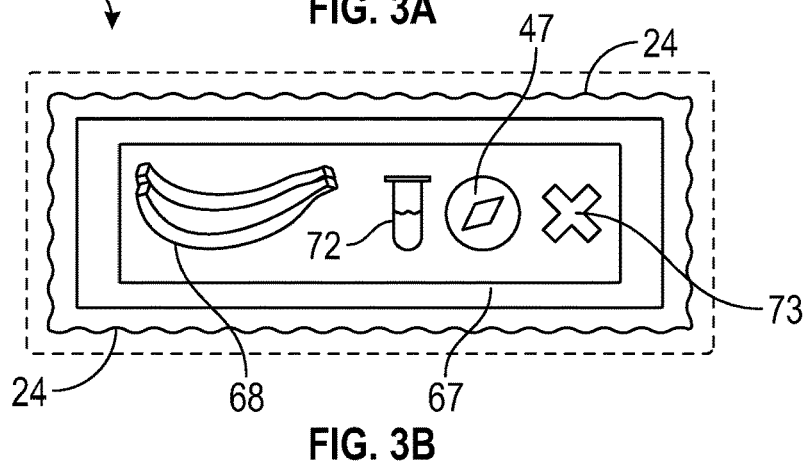
FIG. 3B depicts the shipping container of FIG. 3A containing various perishable items.
Figure 6A:
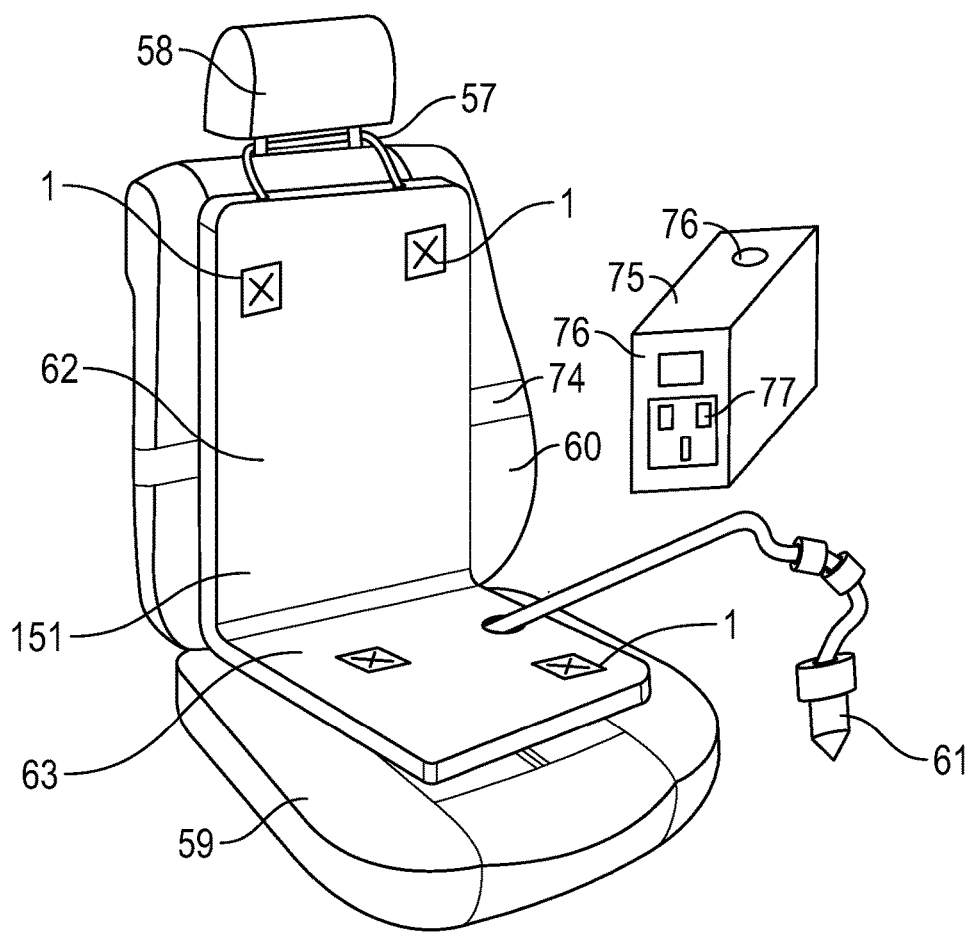
FIG. 6A represents a perspective view of thermoregulation device applied as a car seat cover.
Figure 6B:
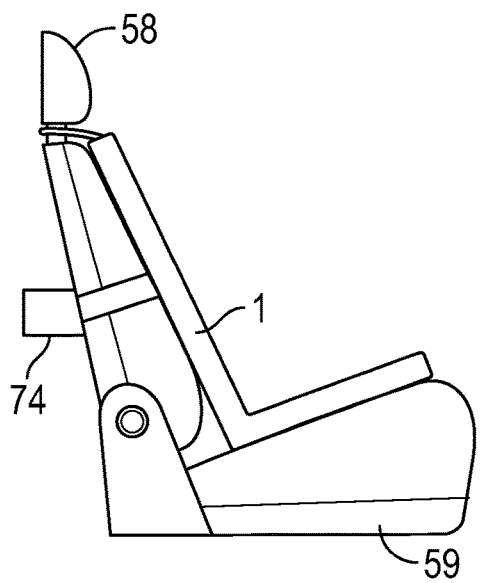
FIG. 6B shows a side view of the car seat cover shown in FIG. 6A.
Figure 7:
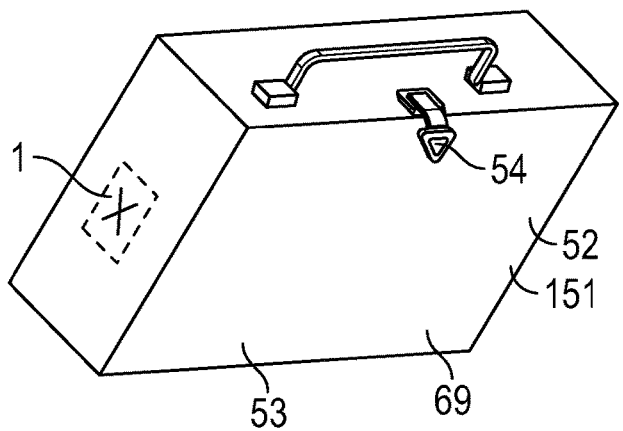
FIG. 7 depicts a transport container comprising a thermoelectric component.
Figure 8:
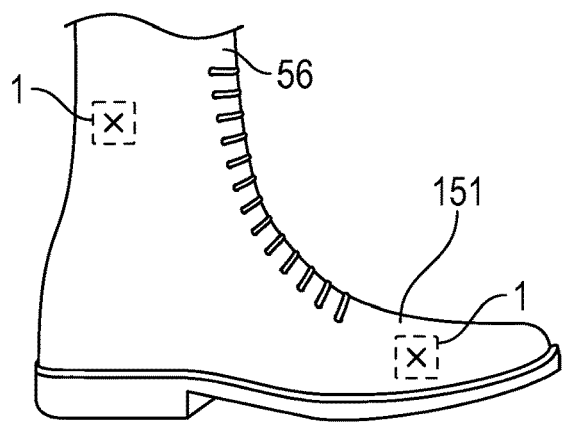
FIG. 8 depicts an orthopedic boot as an embodiment of a thermoregulation device.
Figure 9:
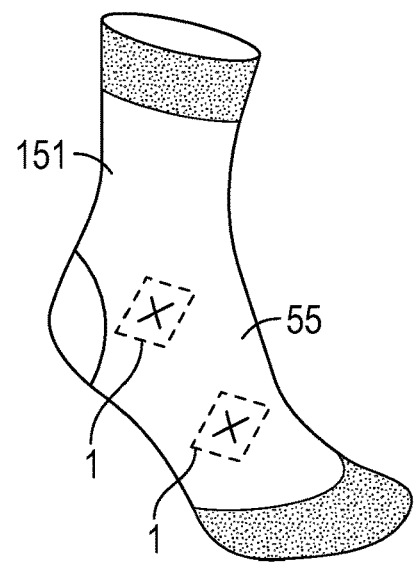
FIG. 9 depicts a sock as an embodiment of a thermoregulation device.
Figure 10:
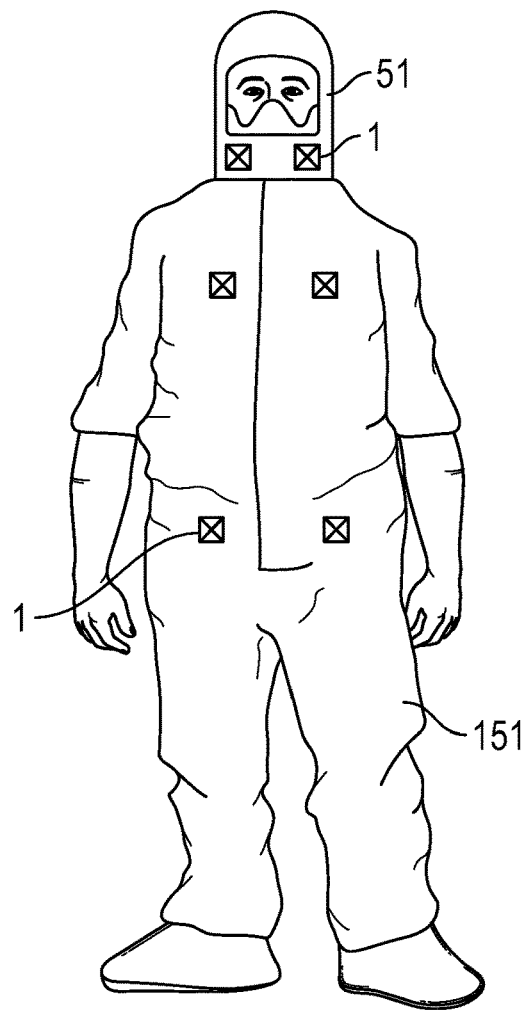
FIG. 10 depicts a hazardous conditions uniform as an embodiment of a circumferential thermoregulation device.
Figure 11:
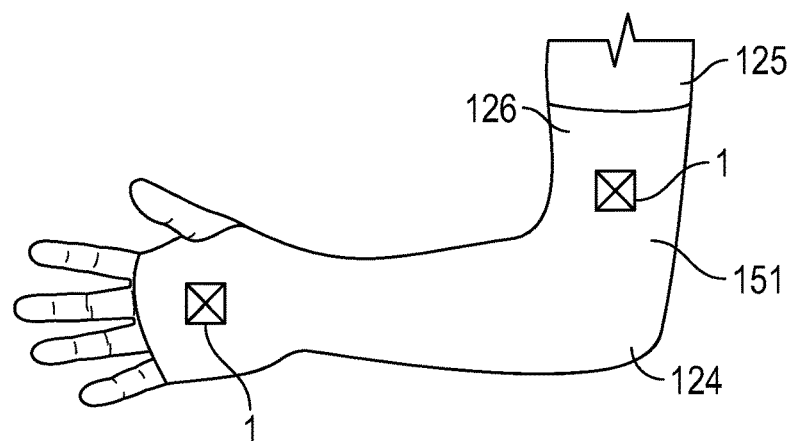
FIG. 11 depicts an orthopedic cast as an embodiment of a circumferential thermoregulation device.
Figure 12A:
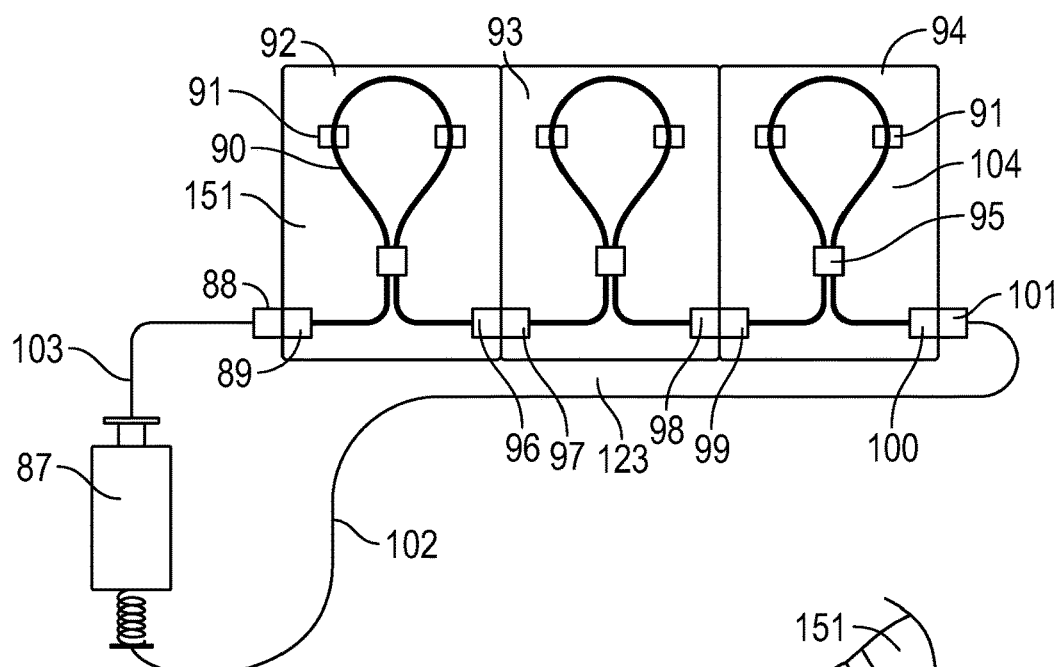
FIG. 12A depicts a bandage with a plurality of interlocking panels as an embodiment of a thermoregulation device.
Figure 12B:
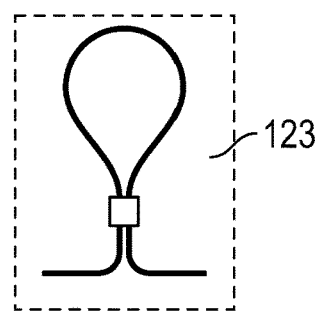
FIG. 12B depicts the wire unit of the panels shown in the bandage depicted in FIG. 12A.
Figure 13:
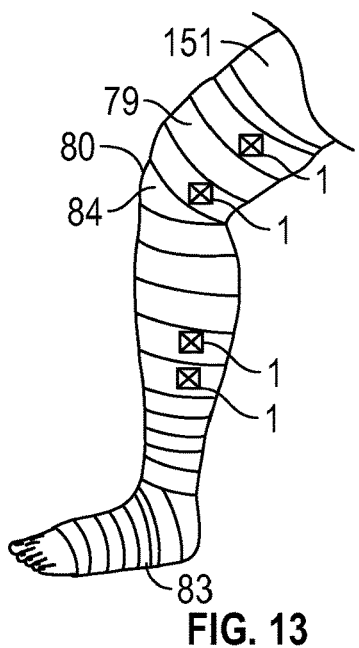
FIG. 13 depicts a cast as an embodiment of a thermoregulation device.
Figure 14:
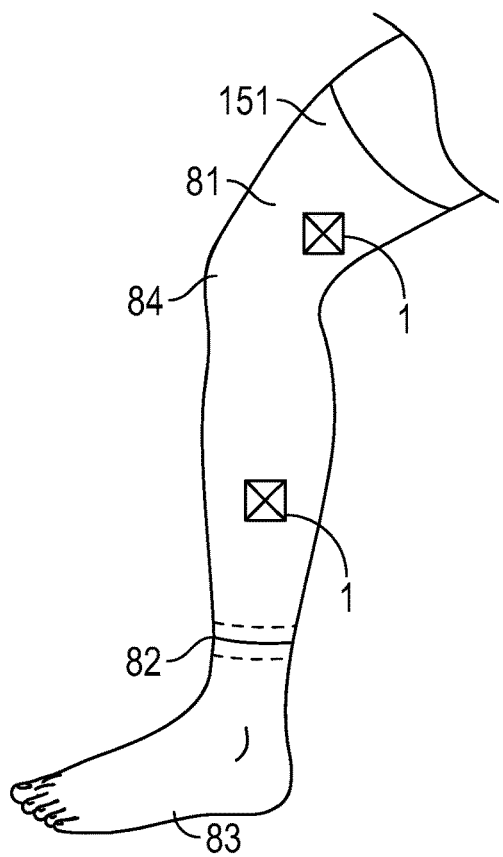
FIG. 14 depicts a stockinette as an embodiment of a thermoregulation device.
Figure 15:
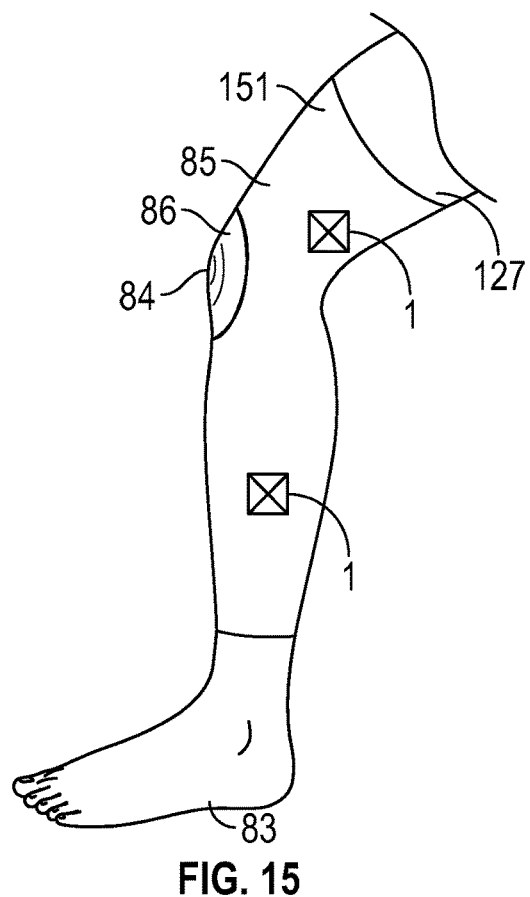
FIG. 15 depicts a knee brace as an embodiment of a thermoregulation device.
Figure 16:
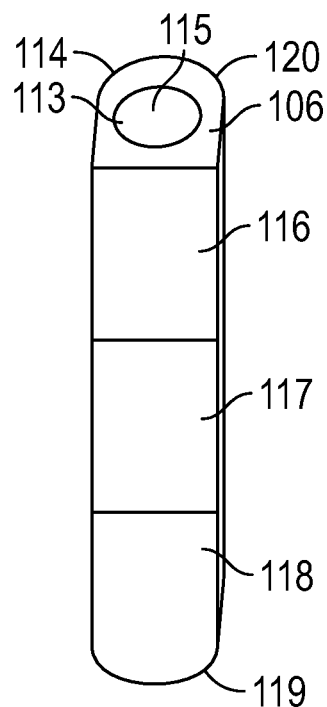
FIG. 16 depicts an embodiment of the sleeve having an opening and three continuous sections without the presence of couplers between the sections.
Figure 17:
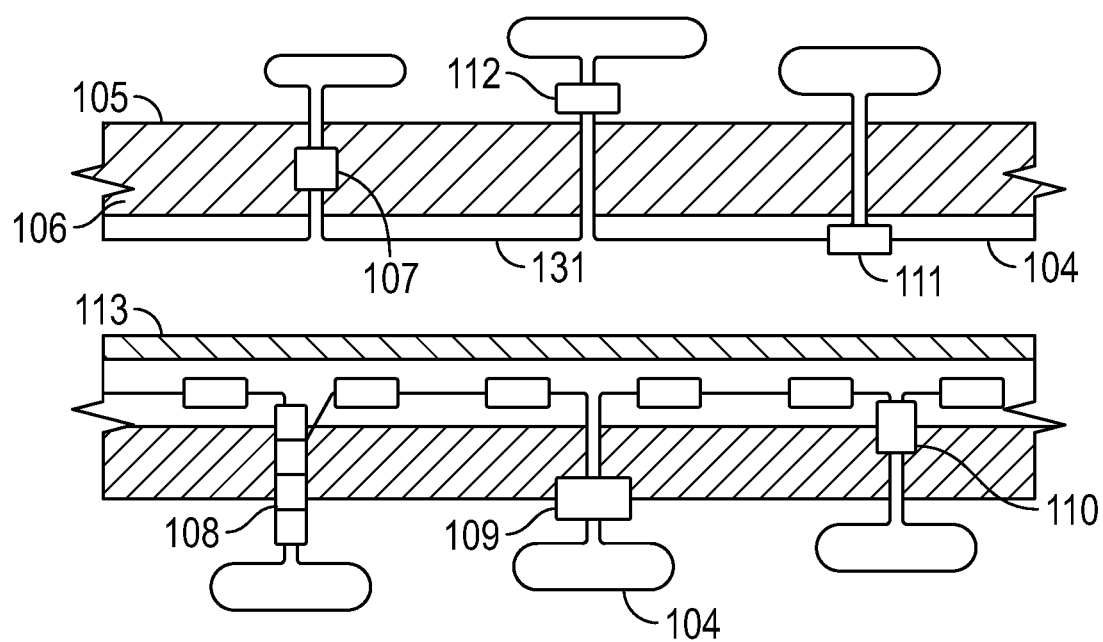
FIG. 17 shows a schematic view of a sleeve without couplers between sections.
Figure 18:
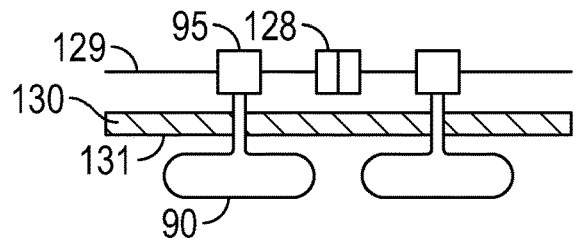
FIG. 18 shows a schematic view of a sleeve with couplers between sections.
Figure 19:
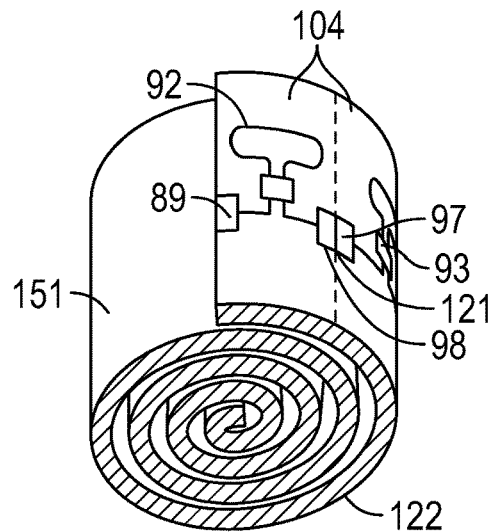
FIG. 19 shows the bandage of FIG. 12A as a roll.
Figure 20:
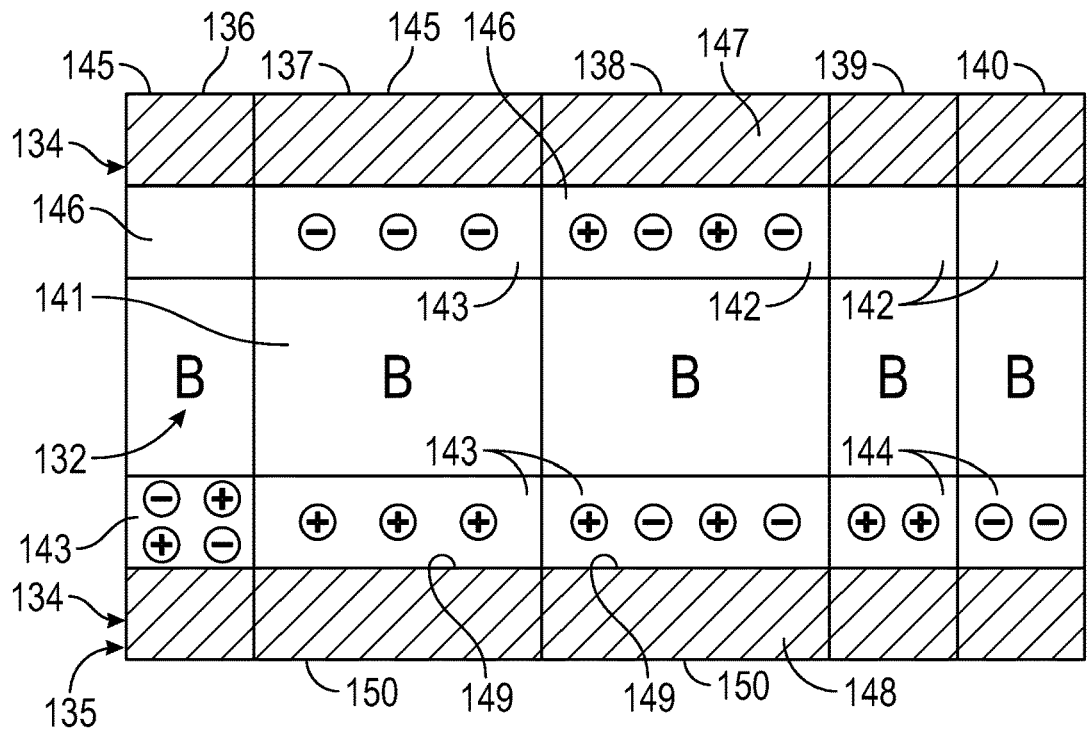
FIG. 20 shows a schematic view of a cross section of a circumferential thermoregulation device applied to a body tissue.

Certain embodiments are described in detail by FIGS. 1-20. The following is a description of each element provided by the figures.

1. Thermoelectric Component.
2. Sleeve.
3. Strap
4. Sensors
5. Indicator
6. Thermoelectric component embedded in the sleeve wall
7. Thermoelectric component inside of the sleeve
8. Thermoelectric component extending outside the sleeve
9. Thermoelectric component combination.
10. localized applied of heating or cooling to counteract the effects of another localized wet surface
11. extremity
12. brace
13. Distal thermoelectric element
14. Proximal thermoelectric element
15. Temperature gradient
16. Temperature
17. Temperature
18. Head
19. Thermal sensors thermostatic control
20. Container
21. flexible container, e.g. may be envelope
22. adhesive
23. timing mechanism
24. shake protector, e.g. may be bubble wrap
25. open end
26. open end
27. battery
28. power adapter
29. wrist splint
30. vibration mechanism
31. internal body sensor.
32. Power Cord
33. Power Plug
34. Power Cord Adapter
35. Mid point between proximal and distal end
36. wireless controller
37. Timer.
38. Transmitter
39. Receiver
40. headband.
41. Hat
42. Visor
43. Sensor
44. Sensor
45. Sensor
46. Phototherapy
47. Geospatial Mechanism
48. Identifier.
49. Blanket
50. Baby
51. Hazardous Conditions Uniform
52. Rigid Shell
53. Lunchbox
54. Fastener
55. Sock
56. Boot
57. Strap
58. Headrest
59. Seat
60. Seatback
61. Panel
62. Panel
63. Collar
64. Neck Brace
65. Back Brace
66. Strap
67. sleeve to apply cool and or heat to a perishable item
68. Perishable item
69. Outer shell.
70. Closure mechanism
71. Flap
72. Specimen
73. Transported item
74. Seat Strap
75. Power Console
76. Power Adapter
77. Power Adapter
78. Power Adapter
79. Orthopedic Tape
80. Cast
81. Stockinette
82. Stocking
83. Foot
84. Knee
85. Knee brace
86. Window
87. Power source
88. Coupler
89. Coupler
90. Wire
91. Positioner
92. Panel
93. Panel
94. Panel
95. —not included—
96. Coupler
97. Coupler
98. Coupler
99. Coupler
100. Coupler
101. Coupler
102. Power Line
103. Power Line
104. Thermoelectric String
105. Sleeve
106. Sleeve Wall
107. Conductor
108. Conductor
109. Conductor
110. Conductor
111. Conductor
112. Conductor
113. Layer
114. Sleeve
115. Sleeve Opening
116. Sleeve Section
117. Sleeve Section
118. Sleeve Section
119. Sleeve End
120. Sleeve End
121. Segment Margin 122. Panel Roll
123. Wire Unit
124. Elbow
125. Upper Arm
126. Orthopedic Appliance for Arm
127. Thigh
128. Couplers
129. A wall
130. A surface
131. Multiple Units without Coupler
132. Portion of Body Part
133. Thermoregulation
134. Sleeve Layer
135. Panel Layer
136. Segment
137. Segment
138. Segment
139. Segment
140. Segment
141. Thermoregulated Cavity
142. Body Surface
143. Body Surface
144. Body Surface
145. Sleeve Surface
146. Sleeve Surface
147. Sleeve Wall
148. Sleeve Wall
149. Sleeve Surface
150. Sleeve Surface
151. Thermoregulation Device

What is claimed is:

1. A thermal orthopedic treatment system comprising:
a power source (87);
a first wire (103) electrically coupled to the power source (87) and terminated by a first power source coupling (88);
a second wire (102) electrically coupled to the power source (87) and terminated by a second power source coupling (101); and
a thermoregulation device (151) comprising a plurality of thermoelectric panels (92, 93, 94) arranged in series;
wherein each of the plurality of thermoelectric panels (93) comprises:
a first panel electrical input coupling (97) configured to reversibly connect to either of the first power source coupling (88) and a second panel electrical output coupling (96) of a second of the plurality of thermoelectric panels (92);
a first panel electrical output coupling (98) configured to reversibly connect to either of the second power source coupling (101) and a third panel electrical input coupling (99) of a third of the plurality of thermoelectric panels (94);
a first panel margin (121) to secure the at least one of the plurality of thermoelectric panels (93) to the second of the plurality of thermoelectric panels (92);
a second panel margin (121) to secure the at least one of the plurality of thermoelectric panels (93) to the third of the plurality of thermoelectric panels (94); and
a thermoelectric element (90) electrically coupled to both of the first panel electrical input coupling (97) and the first panel electrical output coupling (98).

2. A method for treating injured body tissue, pain or vascular disorders, the method comprising:
applying the thermoregulation device of claim 1 to a body tissue; and
regulating the temperature of the body tissue by controlling the thermoregulation device.

3. The method of claim 2, wherein regulating the temperature of the body tissue comprises maintaining the body tissue at a predetermined temperature for a period of time.

4. The method of claim 2, wherein regulating the temperature of the body tissue comprises maintaining at least a portion of the body tissue at a series of predetermined temperatures for a period of time.

5. The method of claim 2, wherein regulating the temperature of the body tissue comprises generating a thermal gradient along at least a portion of the body tissue.

6. The method of claim 2, wherein regulating the temperature of the body tissue comprises modulating the application of heat or cooling in response to a measured non-thermal body parameter, wherein the non-thermal body parameter comprises a perfusion parameter, a color parameter, a pain parameter, a moisture parameter, a pressure parameter, or any combination thereof.

7. The system of claim 1, wherein the thermoelectric element comprises a cooling element.

8. The system of claim 1, wherein the thermoelectric element comprises individual conductors that are (i) compacted in cross section inside the thermoelectric panel and (ii) expanded in at least one dimension outside the panel.

9. The system of claim 1, wherein the plurality of thermoelectric panels comprises three or more thermoelectric panels.

10. The system of claim 1, wherein one or more of the plurality of thermoelectric panels can be uncoupled from the remaining plurality of thermoelectric panels, and the remaining plurality of thermoelectric panels configured to provide thermoelectric heating or cooling separately from the uncoupled one or more of the plurality of thermoelectric panels.

11. The system of claim 10, wherein the uncoupled one or more of the plurality of thermoelectric panels is also capable of providing thermoelectric heating or cooling.

12. The system of claim 1, wherein the plurality of thermoelectric panels is configured to be positioned along an axis of the injured tissue.

13. The system of claim 1, wherein the plurality of thermoelectric panels is configured to be positioned circumferentially around a longitudinal axis of an extremity.

14. The system of claim 1, wherein each of the plurality of thermoelectric panels comprises a flexible material configured to circumferentially wrap around an extremity and contact the injured tissue.

15. The system of claim 1, further comprising a vibrator element for providing vibration therapy.

16. The system of claim 1, further comprising an orthopedic positioner selected from a brace, a sleeve, a cast, a splint, a wound dressing, a stocking, a sock, and a compression stocking.

17. The system of claim 16, wherein the orthopedic positioner is an adjustable sleeve.

18. The system of claim 16, wherein the orthopedic positioner is a cast.

19. The system of claim 1, wherein each of the plurality of thermoelectric panels is an interlocking panel.

20. The system of claim 18, wherein the plurality of thermoelectric panels is a bandage roll.

21. The system of claim 1, wherein the thermoelectric element comprises a heating element.

22. The system of claim 1, wherein the thermoelectric element comprises a cooling element and a heating element.

* * * * *